US012636273B2

(12) United States Patent     (10) Patent No.:   US 12,636,273 B2

Choate et al.     (45) Date of Patent:    May 26, 2026

---

(54) COMPOSITIONS FOR PATHOGENESIS-DIRECTED THERAPY AND TREATMENTS OF SKIN DISEASES AND DISORDERS

(71) Applicant: YALE UNIVERSITY, New Haven, CT (US)

(72) Inventors: Keith Choate, New Haven, CT (US); Lihi Atzmony, New Haven, CT (US)

(73) Assignee: YALE UNIVERSITY, New Haven, CT (US)

( * ) Notice: Subject to any disclaimer, the term of this patent is extended or adjusted under 35 U.S.C. 154(b) by 948 days.

(21) Appl. No.: 17/618,215

(22) PCT Filed: Jun. 10, 2020

(86) PCT No.: PCT/US2020/037003

§ 371 (c)(1),
(2) Date: Dec. 10, 2021

(87) PCT Pub. No.: WO2020/252025

PCT Pub. Date: Dec. 17, 2020

(65) Prior Publication Data

US 2022/0168270 A1    Jun. 2, 2022

Related U.S. Application Data

(60) Provisional application No. 62/859,750, filed on Jun. 11, 2019.

(51) Int. Cl.
| | |
|---|---|
| *A61K 31/366* | (2006.01) |
| *A61K 9/00* | (2006.01) |
| *A61K 45/06* | (2006.01) |
| *A61P 17/12* | (2006.01) |

(52) U.S. Cl.
CPC .......... *A61K 31/366* (2013.01); *A61K 9/0014* (2013.01); *A61K 45/06* (2013.01); *A61P 17/12* (2018.01)

(58) Field of Classification Search
CPC ...... A61K 31/366; A61K 9/0014; A61P 17/12
See application file for complete search history.

(56) References Cited

U.S. PATENT DOCUMENTS

2002/0010128 A1*   1/2002   Parks ..................... A61K 47/14
                                        514/729

OTHER PUBLICATIONS

Paller et al. (Journal of Investigative Dermatology (2011) 131, 2242-2248) (Year: 2011).*
Zhang et al. (ELife, 2015, vol. 4, p. 1-16) (Year: 2015).*
Khalil et al. (JAMA Dermatol. 2018;154(11):1320-1323) (Year: 2018).*

* cited by examiner

*Primary Examiner* — James D. Anderson
(74) *Attorney, Agent, or Firm* — Riverside Law LLP

(57) ABSTRACT

The present invention relates to compositions comprising at least one lipid-lowering drug or a derivative thereof for the treatment of skin diseases or disorders. In various aspects of the invention, the composition further comprises at least one lipid or a derivative thereof.

11 Claims, 7 Drawing Sheets

Subjects characteristics

| Subject ID | Age | Age of porokeratosis onset | Porokeratosis subtype | History of skin cancer |
|---|---|---|---|---|
| FP100-1 | 36 | 18 yo | DSAP | No |
| FP100-6 | 40 | 16 yo | PPPD | No |
| FP100-9 | 53 | 19 yo | PPPD | SCC |
| LP-1 | 20 | Birth | LP | No |
| LP-2 | 5 | Birth | LP | No |

Abbreviations: DSAP: disseminated superficial actinic porokeratosis, LP: linear porokeratosis, PPPD: porokeratosis palmaris et plantaris disseminata, SCC: squamous cell carcinoma

Figure 3

Genetic analysis of included subjects

| Subject ID | Germline Mutation | # of reads in blood | | # of reads in affected tissue | | Somatic Mutation | # of reads in blood | | # of reads in affected tissue | |
|---|---|---|---|---|---|---|---|---|---|---|
| | | Ref. | Non ref. | Ref. | Non ref. | | Ref. | Non ref. | Ref. | Non ref. |
| LP1 | PMVK c.79G>T, p.E27X | 77 | 60 | 86 | 88 | PMVK c.379C>T, p.Q127X | 113 | 0 | 119 | 34 |
| LP2 | PMVK c.329G>A, p.R110Q | 21 | 15 | 16 | 61 | CN-LOH Chr1:1163Mb-248Mb* | N/A | N/A | N/A | N/A |
| FP100-1 | MFD c.70+5G>A | 8 | 10 | 44 | 42 | Not found | | | | |
| FP100-6 | MFD c.70+5G>A | 18 | 12 | 30 | 31 | Not found | | | | |
| FP100-9 | MFD c.70+5G>A | 16 | 15 | N/A | N/A | N/A | N/A | N/A | N/A | N/A |

*PMVK spans Chr1:154,897,208-154,909,484

CN-LOH = copy-neutral loss of heterozygosity; N/A = not applicable, ref reference.

Figure 4

COMPOSITIONS FOR PATHOGENESIS-DIRECTED THERAPY AND TREATMENTS OF SKIN DISEASES AND DISORDERS

CROSS-REFERENCE TO RELATED APPLICATIONS

This application is a national phase application filed under 35 U.S.C. § 371 claiming benefit to PCT International Application PCT/US2020/037003, filed Jun. 10, 2020, which claims priority under 35 U.S.C. § 119 (e) to U.S. Provisional Patent Application Ser. No. 62/859,750, filed Jun. 11, 2019, the disclosures of which are incorporated herein by reference in their entireties.

STATEMENT REGARDING FEDERALLY SPONSORED RESEARCH OR DEVELOPMENT

This invention was made with government support under R01AR071491 awarded by the National Institutes of Health/National Institute of Arthritis and Musculoskeletal and Skin Diseases. The government has certain rights in the invention.

BACKGROUND OF THE INVENTION

Porokeratosis is a heterogynous group of keratinization disorders sub-classified based on clinical appearance. Examples of porokeratosis subtypes are disseminated superficial actinic porokeratosis (DSAP), disseminated superficial porokeratosis (DSP), porokeratosis of Mibelli, porokeratosis palmaris et plantaris disseminata (PPPD), and linear porokeratosis (LP). All variants share the histopathological feature of a cornoid lamella (CL), a vertical column of parakeratosis situated above dyskeratotic cells within the granular layer (Biswas A, 2015, Am J Dermatopathol 37:145-155). Familial case with an autosomal dominant mode of inheritance, as well as sporadic cases have been described (Wang J et al., 2016, Sci Rep 6:24226; Zhang S-Q et al., 2012, Nat Genet 44:1156-1160; Leng Y et al., 2018, J Dermatol 45:862-866). DSAP is the most common subtype of porokeratosis, although its exact prevalence is unknown. It usually affects individuals in their 30s and 40s with a slight female predominance. Lesions appear on sun-exposed areas as asymptomatic or pruritic pink to brown papules or plaques with a raised hyperkeratotic border and an atrophic, sometimes hypopigmented center.

Porokeratosis is considered a premalignant condition with an overall malignant transformation rate of 7.5% (Sasson M et al., 1996, Dermatol Surg 22:339-342). The most common reported malignancy is squamous cell carcinoma (SCC), but basal cell carcinomas and melanomas have also been reported (Schierbeck J et al., 2019, Acta Derm Venereol 99:360-369; Al-Haseni A et al., 2018, Dermatol Ther e12552). Although all subtypes of porokeratosis have an increased risk of skin cancer, linear, large and long-standing lesions were reported to have higher risk (Sasson M et al., 1996, Dermatol Surg 22:339-342).

Current treatments for porokeratosis are focused on lesion destruction as in other clonal keratinocytic disorders, or reducing the scale and inflammation. Examples of the former include cryotherapy, photodynamic therapy (PDT), $CO_2$ lasers and 5-fluorouracil, and for the latter are acitretin, topical corticosteroids and vitamin D analogs (Weidner T et al., 2017, Am J Clin Dermatol 18:435-449). These approaches are often ineffective and pricy.

Over the past few years heterozygous germline mutations of the mevalonate pathway genes MVK, PMVK, MVD (MIM 603236) and FDPS (MIM 134629) were identified in familial and sporadic porokeratosis, while second hit mutations were identified in linear porokeratosis, proving the role of Knudson phenomena as well as the necessity of diminished enzymatic activity of PMVK or MVD in order to develop porokeratosis skin lesions (Zhang S-Q et al., 2012, Nat Genet 44:1156-1160; Zhang Z et al., 2015, eLife 4:e06322; Atzmony et al., 2019, JAMA Derm., 155:548-555; Kubo A et al., 2019, J. Invest. Dermatol., 139:2458-2466.e9).

In the first committed step of the mevalonate pathway hydroxymethylglutaryl coenzyme A reductase (HMGCR), which is inhibited by statins, converts HMG-CoA to mevalonate. Mevalonate is further metabolized to isopentenyl pyrophosphate (IPP) by sequential rate limiting steps catalyzed by MVK, PMVK and MVD. IPP is the building block of a variety of isoprenoids compound including cholesterol, dolichol ubiquitone and the isoprenoids farnesol and geranylgeraniol which are essential for cell growth and differentiation, gene expression, cytoskeleton assembly and post translational modification of proteins involved in intracellular signaling (Goldstein J L et al., 1990, Nature 343:425-430).

Cholesterol is one of the components of the extracellular lipid matrix in the stratum corneum, playing an essential role in providing and maintaining skin barrier. Depletion of cholesterol has been reported to result in increased sensitivity of keratinocytes to stimuli driving apoptosis (Calay D et al., 2010, J Invest Dermatol. 130:1136-1145). Premature apoptosis and dysregulated differentiation of keratinocytes have been identified in several types of porokeratosis (Wang J et al., 2016, Sci Rep. 6:24226; Shen C-S et al., 2002, Br J Dermatol 147:498-502), so perhaps loss of function mutations in MVK, PMVK, MVD and FDPS may result in cholesterol deficiency in porokeratosis affected skin, contributing to disease pathogenesis and phenotype (Wang J et al., 2016, Sci Rep. 6:24226; Shen C-S et al., 2002, Br J Dermatol 147:498-502). Porokeratosis phenotype can reflect not only the deficiency of metabolic pathway end products but also the accumulation of toxic metabolites (Zettersten E et al., 1998, J Invest Dermatol 111:784-790; Elias P M et al., 2008, J Lipid Res 49:697-714). This has been demonstrated in other inherited metabolic diseases (Zettersten E et al., 1998, J Invest Dermatol 111:784-790; Elias P M et al., 2008, J Lipid Res 49:697-714).

These recent advances in understanding of the pathogenesis of porokeratosis, open the door for topical pathogenesis- or mechanism-directed therapy that aims to correct the metabolic anomalies that result from diminished mevalonate-pathway enzymes activity. A therapeutic approach of toxic metabolites accumulation inhibition and essential end-product replenishment has been utilized in CHILD syndrome, an X-linked dominant disorder of distal cholesterol metabolism, where topical application of lovastatin, an HMG-CoA inhibitor and cholesterol led to significant improvement of skin lesions, whereas application of cholesterol only did not correct the phenotype (Paller A S et al., 2011, J Invest Dermatol 131:2242-2248). Topical application of lovastatin/cholesterol bypasses the first-pass effect of statins metabolism by the liver as well as the intrahepatic incorporation of cholesterol into lipoprotein particles, which are unable to access the skin without low density proteins (Ponec M et al., 1992, J Invest Dermatol 98(6 Suppl):50S-56S).

Thus, there is a need in the art for treatments of skin diseases and disorders, such as porokeratosis, that replenish cholesterol and/or block accumulation of mevalonate pathway toxic metabolites. The present invention addresses this unmet need in the art.

SUMMARY OF THE INVENTION

The present invention relates to compositions comprising at least one lipid-lowering drug or a derivative thereof. In one embodiment, the lipid-lowering drug or derivative thereof is a 3-hydroxy-3-methyl-glutaryl-coenzyme A (HMG-CoA) reductase inhibitor. In one embodiment, the HMG-CoA reductase inhibitor is atorvastatin, fluvastatin, lovastatin, pravastatin, rosuvastatin, simvastatin, pitavastatin, or any combination thereof. In one embodiment, the lipid or derivative thereof is a cholesterol.

In some embodiments, the lipid-lowering drug or derivative thereof is present in an amount of about 2%. In various embodiments, the lipid-lowering drug or derivative thereof is lovastatin present in an amount of about 2%

In various aspects, the invention relates to compositions further comprising at least one lipid or a derivative thereof. Thus, in some aspect, the invention relates to compositions comprising at least one lipid or a derivative thereof and at least one lipid-lowering drug or a derivative thereof. In one embodiment, the composition comprises at least one lipid or a derivative thereof and at least one HMG-CoA reductase inhibitor or a derivative thereof. In one embodiment, the lipid or a derivative thereof is cholesterol.

In some embodiments, the lipid or derivative thereof is present in an amount of about 0.1% to about 25% and the lipid-lowering drug or derivative thereof is present in an amount of about 0.1% to about 25%. In some embodiments, the lipid or derivative thereof is present in an amount of about 1% to about 10% and the lipid-lowering drug or derivative thereof is present in an amount of about 1% to about 10%. In some embodiments, the lipid or derivative thereof is present in an amount of about 2% and the lipid-lowering drug or derivative thereof is present in an amount of about 2%. In various embodiments, the lipid or derivative thereof is cholesterol present in an amount of about 2% and the lipid-lowering drug or derivative thereof is lovastatin present in an amount of about 2%.

In various embodiments, the composition further comprises one or more pharmaceutically acceptable carriers or excipients. In various embodiments, the composition is a gel, an ointment, a cream, an emulsion, a suspension, or any combination thereof.

The present invention also relates to a method of preventing or treating skin diseases or disorders.

In one aspect, the present invention also relates to a method of blocking or reducing mevalonate pathway in a subject in need thereof.

In another aspect, the present invention relates to a method of blocking or reducing accumulation of at least one mevalonate pathway metabolite in a subject in need thereof.

In various embodiments, the method comprises administering a therapeutically effective amount of any composition described herein to a subject in need thereof. In some embodiments, the composition comprises at least one lipid-lowering drug or a derivative thereof. In some embodiments, the composition comprises at least one lipid or a derivative thereof and at least one lipid-lowering drug or a derivative thereof.

In various aspects of the invention, the composition is administered topically. In some embodiments, the composition is administered at least one time per day. In some embodiments, the composition is administered at least one time per day for a duration of 6 months. In some embodiments, the composition is administered one time per day for a duration of 4 to 6 weeks. In some embodiments, the composition is administered two times per day for a duration of 4 to 6 weeks.

In various embodiments, the skin disease or disorder is associated with a MVD mutation, a MVK mutation, a PMVK mutation, a FDPS mutation, or any combination thereof. In one embodiment, the skin disease or disorder is keratinization disease or disorder. In one embodiment, the skin disease or disorder is inflammatory skin disease or disorder. In one embodiment, the skin disease or disorder is precancerous skin lesion. In one embodiment, the skin disease or disorder is cancerous skin lesion. In some embodiments, the skin disease or disorder is inflammatory skin disease or disorder, precancerous skin lesion, cancerous skin lesion, keratinization disease or disorder, or any combination thereof. In one embodiment, the keratinization disease or disorder is porokeratosis. In some embodiments, the porokeratosis is plaque-type porokeratosis (porokeratosis of Mibelli), disseminated superficial actinic porokeratosis (DSAP), disseminated superficial porokeratosis (DSP), porokeratosis palmaris et plantaris disseminate (PPPD), linear porokeratos (LP), punctate porokeratosis, porokeratosis plantaris discrete, porokeratosis ptychotropica, porokeratoma, solar facial porokeratosis, hyperkeratotic porokeratosis, or any combination thereof.

In various aspects of the invention, the method is a pathogenesis-directed therapy. In various embodiments, the composition is administered in combination with another therapeutic agent.

BRIEF DESCRIPTION OF THE DRAWINGS

The following detailed description of various embodiments of the invention will be better understood when read in conjunction with the appended drawings. For the purpose of illustrating the invention, there are shown in the drawings illustrative embodiments. It should be understood, however, that the invention is not limited to the precise arrangements and instrumentalities of the embodiments shown in the drawings.

FIG. 2A and FIG. 2B, depicts representative clinical improvements in subjects with DSAP and PPPD with topical application of lovastatin/cholesterol. FIG. 2A depicts representative example of a treated skin of FP100-1.

FIG. 2B depicts representative example of a treated skin of FP2100-9.

FIG. 3 depicts representative characteristics of the representative subjects.

FIG. 4 depicts the representative results of genetic analysis of included subjects.

FIG. 5A depicts representative example of a skin of LP1 subject before treatment. FIG. 5B depicts representative example of a treated hand skin of LP1 subject. FIG. 5C depicts representative example of a skin of LP2 subject before treatment. FIG. 5D depicts representative example of a treated hand skin of LP2 subject.

FIG. 6A depicts representative example of a skin of LP subject before treatment (top) and representative example of a treated skin of LP subject (bottom). FIG. 6B depicts representative example of a skin of LP subject before treatment (top) and representative example of a treated skin of LP subject (bottom).

FIG. 7A depicts representative example of a skin of DSAP subject before treatment. FIG. 7B depicts representative example of a treated skin of DSAP subject.

DETAILED DESCRIPTION

Figure 1:
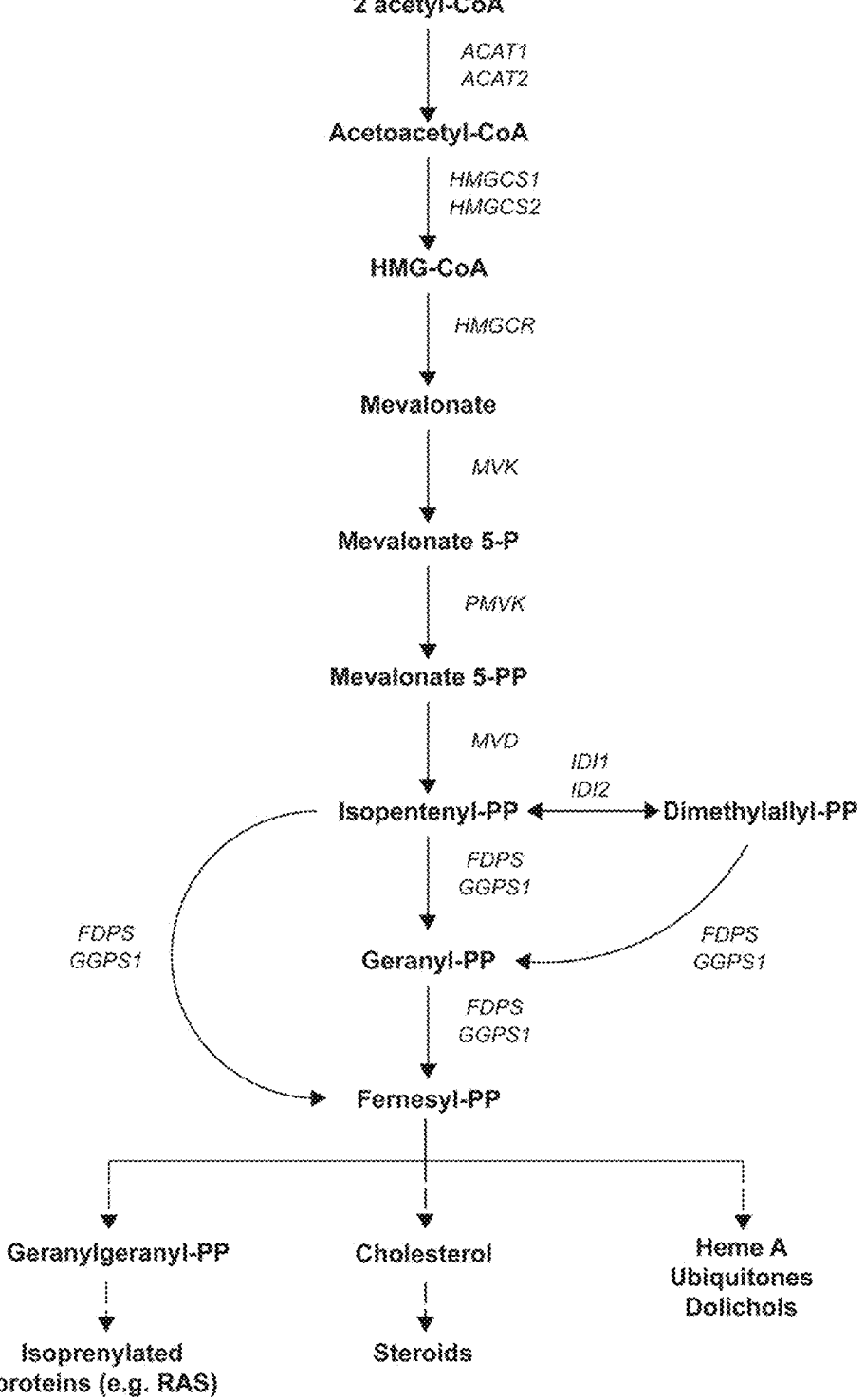
FIG. 1 depicts schematic representation of the Mevalonate pathway. The mevalonate pathway is an essential metabolic pathway that uses acetyl-CoA to produce sterols and isoprenoid metabolites that are essential for a broad range of metabolic processes. Genes previously found to be involved in familial porokeratosis are in bold. Dashed arrows indicate multiple processes.

The present invention is based in part on the discovery that administering a composition comprising at least one lipid-lowering drug (e.g., HMG-CoA reductase inhibitor), and, optionally, further comprising at least one lipid, to a subject in need thereof, alleviates various diseases or disorders. Thus, the invention relates to compositions and methods relating to lipids and/or lipid-lowering drugs (e.g. HMG-CoA reductase inhibitors) that can be used for treating or preventing diseases or disorders, such as skin diseases and disorders.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e. to at least one) of the grammatical object of the article. By way of example, "an element" means one element or more than one element.

The term "about" will be understood by persons of ordinary skill in the art and will vary to some extent depending on the context in which it is used. As used herein when referring to a measurable value such as an amount, a temporal duration, and the like, the term "about" is meant to encompass variations of ±20% or ±10%, more preferably ±5%, even more preferably ±1%, and still more preferably ±0.1% from the specified value, as such variations are appropriate to perform the disclosed methods.

The term "abnormal" when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected) respective characteristic. Characteristics which are normal or expected for one cell or tissue type, might be abnormal for a different cell or tissue type.

A disease or disorder is "treated" if the severity of a sign or symptom of the disease or disorder, the frequency with which such a sign or symptom is experienced by a patient, or both, is reduced. The effect may be prophylactic in terms of completely or partially preventing a disease or disorder, or a sign or symptom thereof and/or may be therapeutic in terms of partially or completely curing a disease and/or adverse effect attributed to the disease.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

The term "inhibit," as used herein, means to suppress or block an activity or function by at least about ten percent relative to a control value. In various embodiments, the activity is suppressed or blocked by at least 50% compared to a comparator value, or by at least 55%, or by at least 60%, or by at least 65%, or by at least 70%, or by at least 75%, or by at least 80%, or by at least 85%, or by at least 90%, or by at least 95%.

The term "active agent" refers to a compound or mixture of compounds, that when added to a composition, tend to produce a particular therapeutic effect.

The term "derivative" refers to a small molecule that differs in structure from the reference molecule, but may retain or enhance the essential properties of the reference molecule and may have additional properties. A derivative may change its interaction with certain other molecules relative to the reference molecule. A derivative molecule may also include a salt, an adduct, tautomer, isomer, or other variant of the reference molecule.

The term "tautomers" are constitutional isomers of organic compounds that readily interconvert by a chemical process (tautomerization).

The term "isomers" or "stereoisomers" refers to compounds, which have identical chemical constitution, but differ with regard to the arrangement of the atoms or groups in space.

As used herein "polymorph" refers to crystalline forms having the same chemical composition but different spatial arrangements of the molecules, atoms, and/or ions forming the crystal.

The term "pharmaceutically acceptable salt" refers to any pharmaceutically acceptable salt, which upon administration to the patient is capable of providing (directly or indirectly) a compound as described herein. Such salts preferably are acid addition salts with physiologically acceptable organic or inorganic acids. Examples of the acid addition salts include mineral acid addition salts such as, for example, hydrochloride, hydrobromide, hydroiodide, sulphate, nitrate, phosphate, and organic acid addition salts such as, for example, acetate, trifluoroacetate, maleate, fumarate, citrate, oxalate, succinate, tartrate, malate, mandelate, methane sulphonate and p-toluenesulphonate. Examples of the alkali addition salts include inorganic salts such as, for example, sodium, potassium, calcium and ammonium salts, and organic alkali salts such as, for example, ethylenediamine, ethanolamine, N,N-dialkylenethanolamine, triethanolamine and basic amino acids salts. However, it will be appreciated that non-pharmaceutically acceptable salts also fall within the scope of the invention since those may be useful in the preparation of pharmaceutically acceptable salts. Procedures for salt formation are conventional in the art.

The term "solvate" in accordance with this invention should be understood as meaning any form of the active compound in accordance with the invention in which said compound is bonded by a non-covalent bond to another molecule (normally a polar solvent), including especially hydrates and alcoholates.

The terms "effective amount" and "pharmaceutically effective amount" refer to a sufficient amount of an agent to provide the desired biological result. That result can be reduction and/or alleviation of a sign, symptom, or cause of a disease or disorder, or any other desired alteration of a biological system. An appropriate effective amount in any individual case may be determined by one of ordinary skill in the art using routine experimentation.

A "therapeutically effective amount" refers to that amount which provides a therapeutic effect for a given disease or disorder and administration regimen. In particular, "therapeutically effective amount" means an amount that is effective to prevent, alleviate or ameliorate the severity and/or frequency of at least one sign or symptom of the disease or disorder, or prolong the survival of the subject being treated, which may be a human or non-human animal. Determination of a therapeutically effective amount is within the skill of the person skilled in the art.

As used herein, the term "pharmaceutical composition" refers to a mixture of at least one compound of the invention with other chemical components and entities, such as carriers, stabilizers, diluents, dispersing agents, suspending agents, thickening agents, and/or excipients. The pharmaceutical composition facilitates administration of the compound to an organism. Multiple techniques of administering a compound exist in the art including, but not limited to, intravenous, aerosol, ophthalmic, and topical administration.

"Pharmaceutically acceptable" refers to those properties and/or substances which are acceptable to the patient from a pharmacological/toxicological point of view and to the manufacturing pharmaceutical chemist from a physical/chemical point of view regarding composition, formulation, stability, patient acceptance and bioavailability.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. "Pharmaceutically acceptable carrier" refers to a medium that does not interfere with the effectiveness of the biological activity of the active ingredient(s) and is not toxic to the host to which it is administered. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, PA), which is incorporated herein by reference.

The terms "patient," "subject," "individual," and the like are used interchangeably herein, and refer to any animal, or cells thereof, whether in vitro or in situ, amenable to the methods described herein. In certain non-limiting embodiments, the patient, subject or individual is a human.

As used herein the term "topical formulation" refers to a formulation that may be applied to an exterior region of the body, including to the skin as well as to mucosal surfaces, including genital, anal, nasal and oral mucosa, to the ear, or the lips. Topical formulations may, for example, be used to confer therapeutic or cosmetic benefit to a patient. Topical formulations can be used for both topical and transdermal administration of substances.

The term "topical administration" is used herein to mean delivery of a substance, such as a therapeutically active agent, into the skin or a localized exterior region of the body, to include skin (intact, diseased, ulcerous, or broken) as well as mucosal surfaces that are usually at least partially exposed to air such as lips, genital and anal mucosa, and nasal and oral mucosa. Topical administration of a drug may often be advantageously applied in, for example, the treatment of various skin disorders or conditions.

The term "intradermal administration" is used to mean administration from the skin exterior into the dermal compartment of the skin such that the concentration of the administered agent in the dermal compartment, relative to the concentration of such agent in the other skin compartments or provided transdermally, is substantially greater than for a comparator formulation. Intradermal administration of an active agent is highly desirable when its mode of action entails interaction with targets in the dermal tissue. As the active agent reaches the dermal compartment by diffusion through the stratum corneum and the epidermis, intradermal administration necessarily entails establishing a concentration of the active agent in the epidermal tissue. Similarly, intradermal administration does not exclude a small percentage of active agent permeating all the way through the skin.

"Instructional material," as that term is used herein, includes a publication, a recording, a diagram, or any other medium of expression which can be used to communicate the usefulness of the lipid, lipid-lowering drug, and/or composition of the invention in the kit for identifying, diagnosing or alleviating or treating the various diseases or disorders recited herein. Optionally, or alternately, the instructional material may describe one or more methods of identifying, diagnosing or alleviating the diseases or disorders in a cell or a tissue of a subject. The instructional material of the kit may, for example, be affixed to a container that contains one or more components of the invention or be shipped together with a container that contains the one or more components of the invention. Alternatively, the instructional material may be shipped separately from the container with the intention that the recipient uses the instructional material and the components cooperatively.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

The present invention is based in part on the discovery that administering a composition comprising at least one lipid-lowering drug (e.g., HMG-CoA reductase inhibitor) to a subject in need thereof, alleviates various diseases or disorders. Thus, the invention relates to compositions and methods relating to lipid-lowering drugs (e.g., HMG-CoA reductase inhibitors) that can be used for treating or preventing diseases or disorders, such as skin diseases and disorders. In some aspects, the invention relates to compositions further comprising at least one lipid or a derivative thereof and methods relating to said compositions that can be used for treating or preventing diseases or disorders, such as skin diseases and disorders.

Compositions

The present invention provides a composition comprising at least one lipid-lowering drug. In one embodiment, the lipid-lowering drug or derivative thereof is a HMG-CoA reductase inhibitor. In one embodiment, the HMG-CoA reductase inhibitor is lovastatin. In one embodiment, the lipid-lowering drug or derivative thereof is a statin. Non-limiting examples of lipid-lowering drugs include atorvastatin, fluvastatin, lovastatin, pravastatin, rosuvastatin, simvastatin, and pitavastatin.

In some embodiments the lipid-lowering drug or derivative thereof is present in a formulation from about 0.1% to about 25%, about 0.1% to about 20%, about 0.1% to about 18%, about 0.1% to about 15%, about 0.1% to about 12.5%, about 0.1% to about 10%, about 0.1% to about 9%, about 0.1% to about 8%, about 0.1% to about 7%, about 0.1% to about 6%, about 0.1% to about 5%, about 0.1% to about 4%, about 0.1% to about 3%, about 0.1% to about 2%, about 0.1% to about 1%, about 0.5% to about 10%, about 0.5% to about 9%, about 0.5% to about 8%, about 0.5% to about 7%, about 0.5% to about 6%, about 0.5% to about 5%, about 0.5% to about 4%, about 0.5% to about 3%, about 0.5% to about 2%, about 0.5% to about 1%, about 1% to about 10%, about 1% to about 9%, about 1% to about 8%, about 1% to about 7%, about 1% to about 6%, about 1% to about 5%, about 1% to about 4%, about 1% to about 3%, about 1% to about 2%, about 1.5% to about 10%, about 1.5% to about 9%, about 1.5% to about 8%, about 1.5% to about 7%, about 1.5% to about 6%, about 1.5% to about 5%, about 1.5% to about 4%, about 1.5% to about 3%, about 1.5% to about 2%, about 2% to about 10%, about 2% to about 9%, about 2% to about 8%, about 2% to about 7%, about 2% to about 6%, about 2% to about 5%, about 2% to about 4%, or about 2% to about 3%. In some embodiments, the lipid-lowering drug or derivative thereof is present in an amount of about 0.1% to about 25%. In some embodiments, the lipid-lowering drug or derivative thereof is present in an amount of about 1% to about 10%. In some embodiments, the amount of the lipid-lowering drug or derivative thereof in the formulation is 0.1%, 0.3%, 0.5%, 0.8%, 1.0%, 1.2%, 1.4%, 1.6%, 1.8% or 2%. In some embodiments, the lipid-lowering drug or derivative thereof is present in an amount of about 2%. In some embodiments, the lipid-lowering drug or derivative thereof is lovastatin present in an amount of about 2%.

In various aspects of the invention, the composition further comprises at least one lipid or a derivative thereof. In one embodiment, the lipid or derivative thereof is a cholesterol. In one aspect, the invention relates to a composition comprising at least one lipid or a derivative thereof and at least one HMG-CoA reductase inhibitor or a derivative thereof.

In some embodiments the lipid or derivative thereof is present in a formulation from about 0.1% to about 25%, about 0.1% to about 20%, about 0.1% to about 18%, about 0.1% to about 15%, about 0.1% to about 12.5%, about 0.1% to about 10%, about 0.1% to about 9%, about 0.1% to about 8%, about 0.1% to about 7%, about 0.1% to about 6%, about 0.1% to about 5%, about 0.1% to about 4%, about 0.1% to about 3%, about 0.1% to about 2%, about 0.1% to about 1%, about 0.5% to about 10%, about 0.5% to about 9%, about 0.5% to about 8%, about 0.5% to about 7%, about 0.5% to about 6%, about 0.5% to about 5%, about 0.5% to about 4%, about 0.5% to about 3%, about 0.5% to about 2%, about 0.5% to about 1%, about 1% to about 10%, about 1% to about 9%, about 1% to about 8%, about 1% to about 7%, about 1% to about 6%, about 1% to about 5%, about 1% to about 4%, about 1% to about 3%, about 1% to about 2%, about 1.5% to about 10%, about 1.5% to about 9%, about 1.5% to about 8%, about 1.5% to about 7%, about 1.5% to about 6%, about 1.5% to about 5%, about 1.5% to about 4%, about 1.5% to about 3%, about 1.5% to about 2%, about 2% to about 10%, about 2% to about 9%, about 2% to about 8%, about 2% to about 7%, about 2% to about 6%, about 2% to about 5%, about 2% to about 4%, or about 2% to about 3%. In some embodiments, the lipid or derivative thereof is present in an amount of about 0.1% to about 25%. In some embodiments, the lipid or derivative thereof is present in an amount of about 1% to about 10%. In some embodiments, the amount of the lipid or derivative thereof in the formulation is 0.1%, 0.3%, 0.5%, 0.8%, 1.0%, 1.2%, 1.4%, 1.6%, 1.8% or 2%. In some embodiments, the lipid or derivative thereof is present in an amount of about 2%. In various embodiments, the lipid or derivative thereof is cholesterol present in an amount of about 2%.

In various embodiments, the composition further comprises one or more pharmaceutically acceptable carriers or excipients. In one embodiment, the composition further comprises a pharmaceutical vehicle. In one embodiment, the composition is solubilized in a pharmaceutical vehicle. In one embodiment, the lipid or derivative thereof is solubilized in a pharmaceutical vehicle. In one embodiment, the lipid-lowing drug or derivative thereof is solubilized in a pharmaceutical vehicle. In one embodiment, the lipid or derivative thereof and the lipid-lowering drug or derivative thereof are solubilized in a pharmaceutical vehicle. In one embodiment, the HMG-CoA reductase inhibitor or derivative thereof is solubilized in a pharmaceutical vehicle. In one embodiment, the lipid or derivative thereof and the HMG-CoA reductase inhibitor or derivative thereof are solubilized in a pharmaceutical vehicle. In one embodiment, the composition has increased bioavailability. In one embodiment, the composition has increased bioavailability when compared to the bioavailability of the same composition in a non-formulated mixture. In one embodiment, the composition has increased solubility. In one embodiment, the composition has improved solubility when compared to the solubility of the same composition in a non-formulated mixture.

In one embodiment, the pharmaceutical vehicle is selected from the group consisting of aqueous buffers, solvents, co-solvents, cyclodextrin complexes, lipid vehicles, and any combination thereof, and optionally further comprising at least one stabilizer, emulsifier, polymer, antioxidant, and any combination thereof.

In one embodiment, the aqueous buffer is selected from the group consisting of aqueous HCl, aqueous citrate-HCl buffer, aqueous NaOH, aqueous citrate-NaOH buffer, aqueous phosphate buffer, aqueous KCl, aqueous borate-KCl—NaOH buffer, PBS buffer, and any combination thereof.

In one embodiment, the aqueous buffer has pH range of pH=0.5-10. In one embodiment, the aqueous buffer has pH range of pH=0.5. In one embodiment, the aqueous buffer has pH=1.0. In one embodiment, the aqueous buffer has pH=2.0. In one embodiment, the aqueous buffer has pH=3.0. In one embodiment, the aqueous buffer has pH=4.0. In one embodiment, the aqueous buffer has pH=5.0. In one embodiment, the aqueous buffer has pH=5.5. In one embodiment, the aqueous buffer has pH=6.0. In one embodiment, the aqueous buffer has pH=7.0. In one embodiment, the aqueous buffer has pH=7.4. In one embodiment, the aqueous buffer has pH=8.0. In one embodiment, the aqueous buffer has pH=9.0. In one embodiment, the aqueous buffer has pH=9.5. In one embodiment, the aqueous buffer has pH=10.0.

In one embodiment, the aqueous buffer has a concentration range of 0.05 N-1.0 N. In one embodiment, the aqueous buffer has a concentration of 0.05 N. In one embodiment, the aqueous buffer has a concentration of 0.1 N. In one embodiment, the aqueous buffer has a concentration of 0.15 N. In one embodiment, the aqueous buffer has a concentration of 0.2 N. In one embodiment, the aqueous buffer has a concentration of 0.3 N. In one embodiment, the aqueous buffer has a concentration of 0.4 N. In one embodiment, the aqueous buffer has a concentration of 0.5 N. In one embodiment, the aqueous buffer has a concentration of 0.6 N. In one embodiment, the aqueous buffer has a concentration of 0.7 N. In one embodiment, the aqueous buffer has a concentration of 0.8 N. In one embodiment, the aqueous buffer has a concentration of 0.9 N. In one embodiment, the aqueous buffer has a concentration of 1.0 N.

In one embodiment, the solvent is selected from the group consisting of acetone, ethyl acetate, acetonitrile, pentane, hexane, heptane, methanol, ethanol, isopropyl alcohol, dimethyl sulfoxide (DMSO), water, chloroform, dichloromethane, diethyl ether, PEG400, Transcutol® (diethylene glycomonoethyl ether), MCT 70, PEG-8 caprylic/capric glycerides, PEG 5 Oleate, propylene glycol, Transcutol® P, PEG400, propylene glycol, glycerol, Captex® 300, Tween® 85, Cremophor® EL, Maisine® 35-1, Maisine® CC, Capmul® MCM, maize oil, and any combination thereof.

In one embodiment, the co-solvent is selected from the group consisting of acetone, ethyl acetate, acetonitrile, pentane, hexane, heptane, methanol, ethanol, isopropyl alcohol, dimethyl sulfoxide (DMSO), water, chloroform, dichloromethane, diethyl ether, PEG400, Transcutol® (diethylene glycomonoethyl ether), MCT 70, PEG-8 caprylic/capric glycerides, PEG 5 Oleate, propylene glycol, Transcutol® P, PEG400, propylene glycol, glycerol, Captex® 300, Tween® 85, Cremophor® EL, Maisine® 35-1, Maisine® CC, Capmul® MCM, maize oil, and any combination thereof.

In one embodiment, the cyclodextrin complexes is selected from the group consisting of methyl-β-cyclodextrin, methyl-γ-cyclodextrin, HP-β-cyclodextrin, HP-γ-cyclodextrin, SBE-β-cyclodextrin, α-cyclodextrin, γ-cyclodextrin,6-O-glucosyl-β-cyclodextrin, and any combination thereof.

In one embodiment, the lipid vehicle is selected from the group consisting of petrolatum, petrolatum-based vehicle, Captex® 300, Tween® 85, Cremophor® EL, Maisine® 35-1, Maisine® CC, Capmul® MCM, maize oil, and any combination thereof. In one embodiment, the lipid vehicle is an oil. In one embodiment, the lipid vehicle is an oil mixture. In one embodiment, the oil mixture comprises at least two oils. In one embodiment, the oil is selected from the group consisting of Captex® 300, Tween® 85, Cremophor® EL, Maisine® 35-1, Maisine® CC, Capmul® MCM, maize oil, and any combination thereof.

In one embodiment, the stabilizer is selected from the group consisting of Pharmacoat® 603, sodium lauryl sulfate (SLS), Nisso HPC-SSL, Kolliphor®, PVP K30, PVP VA 64, and any combination thereof. In one embodiment, the stabilizer is an aqueous solution.

In one embodiment, the polymer is selected from the group consisting of HPMC-AS-MG, HPMC-AS-LG, HPMC-AS-HG, HPMC, HPMC-P-55S, HPMC-P-50, methyl cellulose, HEC, HPC, Eudragit® L100, Eudragit® E100, PEO 100K, PEG 6000, PVP VA64, PVP K30, TPGS, Kollicoat® IR, Carbopol® 980NF, Povocoat® MP, Soluplus®, Sureteric®, Pluronic® F-68, and any combination thereof.

In one embodiment, the antioxidant is selected from the group consisting of Vitamin A, Vitamin C, Vitamin E, Coenzyme Q10, manganese, iodide, melatonin, alpha-carotene, astaxanthin, beta-carotene, canthaxanthin, cryptoxanthin, lutein, lycopene, zeaxanthin, polyphenol antioxidant, flavonoid, flavones, apigenin, luteolin, tangeritin, flavonol, isorhammetin, kaempferol, myricetin, proanthocyanidin, quercetin, flavanone, eriodictyol, hesperetin, naringenin, flavanol, catechin, gallocatechin, gallate esters, epicatechin, epigallocatechin, theaflavin, thearubigin, isoflavone phytoestrogen, daidzein, genistein, glycitein, stilbenoid, resveratrol, pterostilbene, anthocyanin, cyanidin, delphinidin, malvidin, pelargonidin, peonidin, petunidin, chicoric acid, caffeic acid, chlorogenic acid, ferulic acid, cinnamic acid, ellagic acid, ellagitannin, gallic acid, gallotannin, rosmarinic acid, salicylic acid, curcumin, flavonolignan, silymarin, xanthone, eugenol, capsaicin, bilirubin, citric acid, oxalic acid, phytic acid, n-acetylcysteine, R-alpha-lipoic acid, and any combination thereof.

In some embodiments, the compositions of the present invention are formulated with organic solvents. In some embodiments, the composition comprises at least one organic solvent. In some embodiments, the composition comprises at least two organic solvents. In some embodiments, the composition comprises more than two organic solvents. In various embodiments, the organic solvents are substances that are pharmaceutically acceptable for application to the skin. Non-limiting examples of organic solvents include acetic acid; acetone; acetonitrile; 1-butanol; 2-butanol; 2-butanone; tert-butyl alcohol; cyclohexane; diethylene glycol; diethyl ether; diglyme (diethylene glycol); dimethyl ether; 1,2-dimethoxy-ethane (glyme or DME); dimethylformamide (DMF); DMSO; 1,4-dioxane; ethanol; ethyl acetate; ethylene glycol; glycerin; heptane; Hexamethylphosphoramide (HMPA); Hexamethylphosphorous triamide (HMPT); hexane; methanol; methyl t-butyl ether (MTBE); methylene chloride; N-methyl-2-pyrrolidinone (NMP); nitromethane; pentane; petroleum ether (ligroine); 1-propanol; 2-propanol; pyridine; tetrahydrofuran (THF); toluene; triethylamine; o-xylene; m-xylene; and p-xylene.

In some embodiments, the composition comprises different volatilities. In one embodiment, one of the solvents is highly volatile such that the formulation substantially dries relatively quickly on application to the skin of a subject while the second solvent is less volatile and serves to maintain the composition in a substantially solubilized form in order that the composition can continue to be efficiently delivered into the skin of the subject.

In various embodiments, the viscosity of the compositions and formulations is adjusted by incorporation of a thickening agent. In some embodiments, the nature of the thickener and the thickener concentration is chosen so as to produce a formulation of the desired viscosity, as is familiar to one skilled in the art. In some embodiments, the thickening agent is hydroxypropyl cellulose (HPC). In some embodiments, the thickening agent is HY119 hydroxypropyl cellulose NF (CAS number (Spectrum Chemical, Gardena CA) or HPMC. Non-limiting examples of thickening agents include alginic acid, sodium alginate, cellulose polymers, carbomer polymers, carbomer derivatives, cellulose derivatives (such as carboxymethyl cellulose, ethylcellulose, hydroxyethyl cellulose and hydroxypropyl cellulose), hydroxypropyl methyl cellulose (HPMC), polyvinyl alcohol, poloxamers)(Pluronics®, polysaccharides (such as chitosan or the like), natural gums (such as acacia (arabic), tragacanth, xanthan and guar gums), gelatin, bentonite, bee wax, magnesium aluminum silicate)(Veegum®, and the like, as well as mixtures thereof. In some embodiments, the thickening agent is present in wt/wt % of about 0.1% to about 30%. In some embodiments, the thickening agent is present in about 0.1%, 0.2%, 0.3%, 0.4%, 0.5%, 0.6%, 0.7%, 0.8%, 0.9%, 1%, 2%, 3%, 4%, 5%, 10%, 15%, 20%, 25%, or 30%. In some embodiments, the inclusion of a thickener in the formulation results in a gel or a light gel.

In various embodiments, the composition comprises at least one emollient. In some embodiments, the emollient is added to the formulations of the invention so that the formulations can maintain or increase the moisture content of the stratum corneum when the composition is applied to the skin. Emollients may be added to the formulations in addition to the other components described herein, which may also aid in maintaining or improving the skin condition of the user. Emollients are generally separated into two broad classes based on their function. The first class of emollients functions by forming an occlusive barrier to prevent water evaporation from the stratum corneum. The second class of emollients penetrate into the stratum corneum and physically bind water to prevent evaporation. The first class of emollients is subdivided into compounds which are waxes at room temperature and compounds which are liquid oils. The second class of emollients includes those which are water soluble and are often referred to as humectants. Suitable emollients may be selected from any of the classes known in the art. A general list of useful emollients appears, for example, in U.S. Pat. No. 4,478,853 and in EP patent application 0 522 624A1 as well as in the CTFA Cosmetic Ingredient Handbook published by The Cosmetic, Toiletry, and Fragrance Association, Washington D.C. (1992) under the listings "Skin Conditioning agents", "emollients", "humectants", "miscellaneous" and "occlusive."

In various embodiments, the addition of one or more emollients may affect the viscosity and stability of the compositions of the present invention. In some embodiments, a single emollient may be added to the composition. In some embodiments, two or more emollients may be added to the composition. While any of a variety of emollients may be added to the formulations of the present invention, some embodiments will include wax and oil type emollients either alone or combined with water soluble emollients. In some embodiments of the invention, emollient systems can be comprised of humectants in addition to occlusive wax and oil emollients in concentrations that achieve a moisturizing effect and which maintain and improve the condition of the skin upon repeated use. Emollients may be non-comedogenic and chosen to avoid skin irritation or sensitization reactions.

In some embodiments, the composition comprises at least one emollient at a concentration between about 0.1% and about 98% w/w. In some embodiments, the composition comprises at least one emollient at a concentration between about 0.1% and about 20% w/w. In some embodiments, the composition comprises at least one emollient at a concentration between about 0.5% and about 10% w/w. In some embodiments, the composition comprises at least one emollient at a concentration can be between about 1% and about 5% w/w.

In some embodiments, the emollient is a bee wax. In some embodiments, the amount of bee wax in the formulation is about 0.1% to about 98%. In some embodiments, the amount of bee wax in the formulation is about 0.1%, 0.5%, 1%, 2%, 3%, 4%, 4.8%, 4.9%, 5%, 5.1%, 5.2% 13%, 17%, 28%, 29%, 30%, 42%, 45%, 58%, 63%, 75%, 96%, or 98%.

In some embodiments, the composition further comprises at least one (+/−)-limonene; 1,3-butanediol; alpha-terpineol; alpha-tocopherol; ammonium lauryl sulfate; butylene dioxide; caprylic/capric triglycerides; castor oil; cedar leaf oil; ceteareth-12; ceteareth-15; ceteareth-30; ceteth-10; ceteth-2; ceteth-20; ceteth-23; Choleth-24; coco-caprylate/caprate; cocodiethanolamide; corn oil; cyclomethicone; dichlorodifluoromethane; diethanolamine; diethylene glycol monomethyl ether; diethylsebacate; diisopropanolamine; diisopropyl adipate; diisopropyl dilinoleate; dimethyl isosorbide; dimethyl sulfoxide; dipropylene glycol; ethyl acetate; ethyl oleate; ethylene glycol; fatty acids; glycerin; glycerol; glyceryl isostearate; glyceryl laurate; glyceryl monooleate (Capmul® GMO-50); glyceryl monostearate; glyceryl palmitate; glyceryl rincoleate; glyceryl stearate-laureth 23; hexylene glycol; hydrogenated castor oil; imidurea; isoceteth-20; isopropyl alcohol; isopropyl isostearate; isopropyl myristate; isopropyl palmitate; Labrasol®; lactic acid; lauramine oxide; laureth-2; laureth-23; laureth-4; lauric diethanolamide; lauric/myristic diethanolamide; lauryl acetate; lauryl lactate; levulinic acid; L-menthol; Medium chain triglycerides; methoxy PEG-16; methyl alcohol; methyl gluceth-10; methyl laurate; methyl salicylate; myristyl alcohol; myristyl lactate; octyldodecanol; oleic acid; oleth-10; oleth-2; oleth-20; oleth-5; oleyl alcohol; oleyl oleate; PEG-60 hydrogenated castor oil; PEGmethyl ether; pentadecalactone; polyethylene glycol 400; polyoxyl 40 hydrogenated castor oil; polysorbate 20; polysorbate 40; polysorbate 60; polysorbate 65; polysorbate 80; propylene carbonate; propylene glycol; propylene glycol diacetate; propylene glycol dicaprylate; propylene glycol monolaurate; propylene glycol monopalmitostearate; SD alcohol 408; sodium lactate; sodium laureth-2 sulfate; sodium laureth-3 sulfate; sodium lauryl sulfate; sorbitan isostearate; sorbitan monolaurate; sorbitan monooleate; sorbitan monopalmitate; sorbitan monostearate; sorbitan sesquioleate; sorbitan tristearate; sorbitol; soybean oil; spermaceti; squalene; steareth-10; steareth-100; steareth-2; steareth-20; steareth-21; steareth-40; tocopherol; Transcutol®; trideceth-10; triethanolamine lauryl sulfate; trolamine; urea, or any combination thereof.

In one embodiment, the composition is a suspension. In one embodiment, the composition is a nanosuspension. In one embodiment, the composition is an emulsion. In one embodiment, the composition is a solution. In one embodiment, the composition is a liquid formulation. In one embodiment, the composition is a cream. In one embodiment, the composition is a gel. In one embodiment, the composition is a lotion. In one embodiment, the composition is a paste. In one embodiment, the composition is an ointment. In one embodiment, the composition is an emollient. In one embodiment, the composition is a liposome. In one embodiment, the composition a nanosphere. In one embodiment, the composition is a skin tonic. In one embodiment, the composition is a mousse. In one embodiment, the composition is a spray. In one embodiment, the composition is a pack. In one embodiment, the composition is a powder. In one embodiment, the composition is a granule. In one embodiment, the composition is a patch. In one embodiment, the composition an occlusive skin agent.

The pharmaceutical compositions and formulations described herein can be administered to a subject per se, or in pharmaceutical compositions where they are mixed with other active ingredients, as in combination therapy, or suitable carriers or excipient(s). Techniques for formulation and administration of the compounds of the instant application may be found in "Remington's Pharmaceutical Sciences," Mack Publishing Co., Easton, PA, 18$^{th}$ edition, 1990.

The pharmaceutical compositions and formulations disclosed herein may be manufactured in a manner that is itself known, e.g., by means of conventional mixing, dissolving, granulating, levigating, emulsifying, encapsulating, or entrapping processes.

Pharmaceutical compositions and formulations for use in accordance with the present disclosure thus may be formulated in a conventional manner using one or more physiologically acceptable carriers comprising excipients and auxiliaries, which facilitate processing of the active compounds into preparations, which can be used pharmaceutically. Proper formulation is dependent upon the route of administration chosen. Any of the well-known techniques, carriers, and excipients may be used as suitable and as understood in the art; e.g., in Remington's Pharmaceutical Sciences, above.

The compositions may take such forms as suspensions, solutions or emulsions in oily or aqueous vehicles, and may contain formulatory agents such as suspending, stabilizing and/or dispersing agents.

Pharmaceutical compositions, which can be used topically, include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers and/or antioxidants may be added. All formulations for oral administration should be in dosages suitable for such administration.

Capsules are prepared by mixing the compound with an inert pharmaceutical diluent, and filling the mixture into a hard gelatin capsule of appropriate size. Soft gelatin capsules are prepared by machine encapsulation of slurry of the compound with an acceptable vegetable oil, light liquid petrolatum or other inert oil. Fluid unit dosage forms for oral administration such as syrups, elixirs and suspensions can be prepared. The water-soluble forms can be dissolved in an aqueous vehicle together with sugar, aromatic flavoring agents and preservatives to form syrup. An elixir is prepared by using a hydro alcoholic (e. g., ethanol) vehicle with suitable sweeteners such as sugar and saccharin, together with an aromatic flavoring agent. Suspensions can be prepared with an aqueous vehicle with the aid of a suspending agent such as acacia, tragacanth, methylcellulose and the like.

Slow or extended-release delivery systems, including any of a number of biopolymers (biological-based systems), systems employing liposomes, colloids, resins, and other polymeric delivery systems or compartmentalized reservoirs, can be utilized with the compositions described herein to provide a continuous or long term source of therapeutic compound. Such slow release systems are applicable to formulations for delivery via topical administration.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. The suspensions may contain substances, which increase the viscosity of the suspension, such as sodium carboxymethyl cellulose, sorbitol, or dextran. Optionally, the suspension may also contain suitable stabilizers or agents, which increase the solubility of the compounds to allow for the preparation of highly, concentrated solutions.

Alternatively, the active ingredient may be in powder form for constitution with a suitable vehicle, e.g., sterile pyrogen-free water, before use.

Starch microspheres can be prepared by adding a warm aqueous starch solution, e. g., of potato starch, to a heated solution of polyethylene glycol in water with stirring to form an emulsion. When the two-phase system has formed (with the starch solution as the inner phase) the mixture is then cooled to room temperature under continued stirring whereupon the inner phase is converted into gel particles. These particles are then filtered off at room temperature and slurred in a solvent such as ethanol, after which the particles are again filtered off and laid to dry in air. The micro spheres can be hardened by well-known cross-linking procedures such as heat treatment or by using chemical cross-linking agents. Suitable agents include dialdehydes, including glyoxal, malondialdehyde, succinic aldehyde, adipaldehyde, glutaraldehyde and phthalaldehyde, diketones such as butadione, epichlorohydrin, polyphosphate, and borate. Dialdehydes are used to crosslink proteins such as albumin by interaction with amino groups, and diketones form schiff bases with amino groups. Epichlorohydrin activates compounds with nucleophiles such as amino or hydroxyl to an epoxide derivative.

In addition to the formulations described previously, the compounds may also be formulated as a depot preparation. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

A pharmaceutical carrier for the hydrophobic compounds disclosed herein is a co-solvent system comprising benzyl alcohol, a nonpolar surfactant, a water-miscible organic polymer, and an aqueous phase. A common co-solvent system used is a co-solvent system, comprising a solution of 3% w/v benzyl alcohol, 8% w/v of the nonpolar surfactant Polysorbate 80, and 65% w/v polyethylene glycol 300, made up to volume in absolute ethanol. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of Polysorbate 80; the fraction size of polyethylene glycol may be varied; other biocompatible polymers may replace polyethylene glycol, e.g., polyvinyl pyrrolidone; and other sugars or polysaccharides may be used.

Alternatively, other delivery systems for hydrophobic pharmaceutical compounds may be employed. Liposomes and emulsions are well known examples of delivery vehicles or carriers for hydrophobic drugs. Certain organic solvents, such as dimethylsulfoxide, also may be employed, although usually at the cost of greater toxicity. Additionally, the compounds may be delivered using a sustained-release system, such as semipermeable matrices of solid hydrophobic polymers containing the therapeutic agent. Various sustained-release materials have been established and are well known by those skilled in the art. Depending on the chemical nature and the biological stability of the therapeutic reagent, additional strategies for stabilization may be employed.

Many of the compounds used in the pharmaceutical combinations disclosed herein may be provided as salts with pharmaceutically compatible counterions. Pharmaceutically compatible salts may be formed with many acids, including but not limited to hydrochloric, sulfuric, acetic, lactic, tartaric, malic, succinic, etc. Salts tend to be more soluble in aqueous or other protonic solvents than are the corresponding free acids or base forms.

Pharmaceutical compositions suitable for use in the methods disclosed herein include compositions where the active ingredients are contained in an amount effective to achieve its intended purpose. More specifically, a therapeutically effective amount means an amount of compound effective to prevent, alleviate or ameliorate symptoms of disease or prolong the survival of the subject being treated. Determination of a therapeutically effective amount is well within the capability of those skilled in the art, especially in light of the detailed disclosure provided herein.

The exact formulation, route of administration and dosage for the pharmaceutical compositions disclosed herein can be chosen by the individual physician in view of the patient's condition. (See e.g., Fingl et al. 1975, in "The Pharmacological Basis of Therapeutics", Ch. 1 p. 1). Typically, the dose about the composition administered to the patient can be from about 0.5 to 1000 mg/kg of the patient's body weight, or 1 to 500 mg/kg, or 10 to 500 mg/kg, or 50 to 100 mg/kg of the patient's body weight. The dosage may be a single one or a series of two or more given in the course of one or more days, as is needed by the patient. Note that for almost all of the specific compounds mentioned in the present disclosure, human dosages for treatment of at least some condition have been established. Thus, in most instances, the methods disclosed herein will use those same dosages, or dosages that are between about 0.1% and about 500%, or between about 25% and about 250%, or between about 50% and about 100% of the established human dosage. Where no human dosage is established, as will be the case for newly discovered pharmaceutical compounds, a suitable human dosage can be inferred from ED50 or ID50 values, or other appropriate values derived from in vitro or in vivo studies, as qualified by toxicity studies and efficacy studies in animals.

Although the exact dosage will be determined on a drug-by-drug basis, in most cases, some generalizations regarding the dosage can be made. The daily dosage regimen for an adult human patient may be, for example, a topical dose of between 0.1 mg and 2000 mg of each ingredient, preferably between 1 mg and 250 mg, e.g., 5 to 200 mg or a topical, subcutaneous, or intramuscular dose of each ingredient between 0.01 mg and 500 mg, preferably between 0.1 mg and 60 mg, e.g., 0.1 to 40 mg of each ingredient of the pharmaceutical compositions disclosed herein or a pharmaceutically acceptable salt thereof calculated as the free base, the composition being administered 1 to 4 times per day. Thus, the total daily dosage by topical administration will typically be in the range 0.1 to 2000 mg. Suitably the compounds will be administered for a period of continuous therapy, for example for a week or more, or for months or years.

Dosage amount and interval may be adjusted individually to provide plasma levels of the active moiety, which are sufficient to maintain the modulating effects, or minimal effective concentration (MEC). The MEC will vary for each compound but can be estimated from in vitro data. Dosages necessary to achieve the MEC will depend on individual characteristics and route of administration. However, HPLC assays or bioassays can be used to determine plasma concentrations.

Dosage intervals can also be determined using MEC value. Compositions should be administered using a regimen, which maintains plasma levels above the MEC for 10-90% of the time, preferably between 30-90% and most preferably between 50-90%.

In cases of local administration or selective uptake, the effective local concentration of the drug may not be related to plasma concentration.

The amount of composition administered will, of course, be dependent on the subject being treated, on the subject's weight, the severity of the affliction, the manner of administration and the judgment of the prescribing physician.

The pharmaceutical compositions and formulations may be prepared with pharmaceutically acceptable excipients, which may be a carrier or a diluent, as a way of example. Such compositions can be in the form of a capsule, sachet, paper or other container. In making the compositions, conventional techniques for the preparation of pharmaceutical compositions may be used. For example, the compositions disclosed above herein may be mixed with a carrier, or diluted by a carrier, or enclosed within a carrier that may be in the form of an ampoule, capsule, sachet, paper, or other container. When the carrier serves as a diluent, it may be solid, semi-solid, or liquid material that acts as a vehicle, excipient, or medium for the active compound. The compositions disclosed above herein, for use as described above herein can be adsorbed on a granular solid container for example in a sachet. Some examples of suitable carriers are water, salt solutions, alcohols, polyethylene glycols, polyhydroxyethoxylated castor oil, peanut oil, olive oil, lactose, terra alba, sucrose, cyclodextrin, amylose, magnesium stearate, talc, gelatin, agar, pectin, acacia, stearic acid or lower alkyl ethers of cellulose, silicic acid, fatty acids, fatty acid amines, fatty acid mono glycerides and diglycerides, pentaerythritol fatty acid esters, polyoxyethylene, hydroxymethylcellulose, and polyvinylpyrrolidone. Similarly, the carrier or diluent may include any sustained release material known in the art, such as glyceryl monostearate or glyceryl distearate, alone or mixed with a wax. Said compositions may also include wetting agents, emulsifying and suspending agents, preserving agents, sweetening agents or flavoring agents. The compositions for use in the treatment of skin diseases or disorders, described in present invention may be formulated so as to provide quick, sustained, or delayed release of the lipids and/or lipid-lowering drugs disclosed herein after administration to the patient by employing procedures well known in the art.

The pharmaceutical compositions and formulations can be sterilized and mixed, if desired, with auxiliary agents, emulsifiers, salt for influencing osmotic pressure, buffers and/or coloring substances and the like, which do not deleteriously react with the compounds disclosed above herein.

The pharmaceutical compositions and formulations may be prepared, packaged, or sold in the form of a sterile aqueous or oily suspension or solution. This suspension or solution may be formulated according to the known art, and may comprise, in addition to the active ingredient, additional ingredients such as the dispersing agents, wetting agents, or suspending agents described herein. Such sterile formulations may be prepared using a non-toxic diluent or solvent, such as water or 1,3 butane diol, for example. Other acceptable diluents and solvents include, but are not limited to, Ringer's solution, isotonic sodium chloride solution, and fixed oils such as synthetic mono or di-glycerides. Other parentally-administrable formulations which are useful include those which comprise the active ingredient in microcrystalline form, in a liposomal preparation, or as a component of a biodegradable polymer system. Compositions for sustained release or implantation may comprise pharmaceutically acceptable polymeric or hydrophobic materials, such as an emulsion, an ion exchange resin, a sparingly soluble polymer, or a sparingly soluble salt.

The compositions of the invention may, if desired, be presented in a pack or dispenser device, which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions comprising a compound disclosed herein formulated in a compatible pharmaceutical carrier may also be prepared, placed in an appropriate container, and labeled for treatment of an indicated condition.

Treatment

The present invention further relates to a method of preventing or treating a diseases or disorder. In various aspects of the invention, the method is a pathogenesis-directed therapy. In various aspects, the present invention relates to a method of preventing or treating skin diseases or disorders in a subject in need thereof. In some aspects, the present invention relates to a method of replenishing cholesterol in a subject in need thereof. In some aspects, the present invention relates to a method of blocking or reducing mevalonate pathway in a subject in need thereof. In some aspects, the present invention relates to a method of blocking or reducing accumulation of at least one mevalonate pathway metabolite in a subject in need thereof. In some aspects, the present invention relates to a method of blocking or reducing accumulation of at least one mevalonate pathway toxic metabolite in a subject in need thereof.

In some embodiments, the method comprises administering a therapeutically effective amount of a composition to a subject in need thereof. In some embodiments, the composition comprises at least one lipid-lowering drug or a derivative thereof. In some embodiments, the composition comprises at least one lipid or a derivative thereof and at least one lipid-lowering drug or a derivative thereof. In various embodiments, the method comprises administering a therapeutically effective amount of any composition described herein to a subject in need thereof.

In one embodiment, the present invention provides methods for treatment, inhibition, prevention, or reduction of a skin disease or disorder by administering any composition disclosed herein, to a subject in need thereof, optionally in combination with at least one additional agent or therapy. In one embodiment, the disease or disorder is keratinization disease or disorder. In one embodiment, the keratinization disease or disorder is porokeratosis. In one embodiment, the porokeratosis is familial porokeratosis. In one embodiment, the porokeratosis is sporadic porokeratosis. In one embodiment, the porokeratosis is plaque-type porokeratosis (porokeratosis of Mibelli). In one embodiment, the porokeratosis is disseminated superficial actinic porokeratosis (DSAP). In one embodiment, the porokeratosis is disseminated superficial porokeratosis (DSP). In one embodiment, the porokeratosis is porokeratosis palmaris et plantaris disseminate (PPPD). In one embodiment, the porokeratosis is linear porokeratos (LP). In one embodiment, the porokeratosis is punctate porokeratosis. In one embodiment, the porokeratosis is porokeratosis plantaris discrete. In one embodiment, the porokeratosis is porokeratosis ptychotropica. In one embodiment, the porokeratosis is porokeratoma. In one embodiment, the porokeratosis is solar facial porokeratosis. In one embodiment, the porokeratosis is hyperkeratotic porokeratosis. In some embodiments, the porokeratosis is familial porokeratosis, sporadic porokeratosis, plaque-type porokeratosis (porokeratosis of Mibelli), disseminated superficial actinic porokeratosis (DSAP), disseminated superficial porokeratosis (DSP), porokeratosis palmaris et plantaris disseminate (PPPD), linear porokeratos (LP), punctate porokeratosis, porokeratosis plantaris discrete, porokeratosis ptychotropica, porokeratoma, solar facial porokeratosis, hyperkeratotic porokeratosis, or any combination thereof.

In one embodiment, the disease or disorder is associated with a MVD mutation. In one embodiment, the disease or disorder is associated with a MVK mutation. In one embodiment, the disease or disorder is associated with a PMVK mutation. In one embodiment, the disease or disorder is associated with a FDPS mutation. In various embodiments, the disease or disorder is associated with a MVD mutation, a MVK mutation, a PMVK mutation, a FDPS mutation, or any combination thereof.

In one embodiment, the composition is applied topically. In one embodiment, the composition is administered in combination with another therapeutic agent.

In various embodiments, the method comprises administration of a daily topical dose of a composition comprising at least 1 nM, at least 10 nM, at least 100 nM, at least 200 nM, at least 300 nM, at least 400 nM, at least 500 nM, at least 600 nM, at least 700 nM, at least 800 nM, at least 900 nM, at least 1 µM, at least 2 µM, at least 3 µM, least 4 µM, at least 5 µM, at least 6 µM, at least 7 µM, at least 8 µM, at least 9 µM, at least 10 µM, at least 15 µM, at least 20 µM, at least 25 µM, at least 30 µM, at least 35 µM, at least 40 µM, at least 45 µM, at least 50 µM, or more than 50 µM of at least one lipid and/or at least one lipid-lowering drug at least 1 time daily, at least 2 times daily, at least 3 times daily or more than 3 times daily, for at least one week, at least two weeks, at least three weeks, at least one month, at least 2 months, at least 3 months, at least 4 months, at least 5 months, at least 6 months or for more than 6 months.

In various embodiments, the method comprises administration of a daily topical dose of at least 1 mg, at least 10 mg, at least 20 mg, at least 50 mg, at least 100 mg, at least 200 mg, at least 300 mg, at least 400 mg, at least 500 mg, at least 600 mg, at least 700 mg, at least 800 mg, at least 900 mg, at least 1 g, at least 2 g, at least 3 g, at least 4 g, at least 5 g, at least 6 g or more than 6 g of at least one lipid and/or at least one lipid-lowering drug, at least 1 time daily, at least 2 times daily, at least 3 times daily or more than 3 times daily, for at least one week, at least two weeks, at least three weeks, at least one month, at least 2 months, at least 3 months, at least 4 months, at least 5 months, at least 6 months or for more than 6 months.

In various embodiments, the method of treatment is administered in a combination with another treatment or therapy, including, but not limiting to, pharmacotherapy, surgery, radiation, chemotherapy, and any combination thereof. In one embodiment, the method further comprises administering adjuvant radiotherapy to the subject in need thereof.

In some embodiments, the administered compositions of the present invention can increase the number of disease-free days, reduce the severity of a disease or disorder, reduce the risk of developing a disease or disorder, reduce the risk of recurrence of a disease or disorder, or a combination thereof in the subject. The administered compositions of the present invention can increase the number of disease-free days by 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60% or more in the subject as compared to a subject who is not receiving treatment.

The administered compositions of the present invention can reduce the severity of a disease or disorder by 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60% or more in the subject as compared to a subject who is not receiving treatment.

The administered compositions of the present invention can reduce the risk of developing a sign or symptom of a disease or disorder by 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60% or more in the subject as compared to a subject who is not receiving treatment.

22

The administered compositions of the present invention can reduce the risk of recurrence of a disease or disorder by 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60% or more in the subject as compared to a subject who is not receiving treatment.

In some embodiments, the method replenishes cholesterol. In some embodiments, the administered compositions of the present invention can replenish cholesterol, increase the level of cholesterol, or a combination thereof in the subject. The administered compositions of the present invention can replenish cholesterol by 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60% or more in the subject as compared to a subject who is not receiving treatment. The administered compositions of the present invention can increase the level of cholesterol by 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60% or more in the subject as compared to a subject who is not receiving treatment.

In some embodiments, the method blocks or reduces the mevalonate pathway. The administered compositions of the present invention can reduce the mevalonate pathway by 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60% or more in the subject as compared to a subject who is not receiving treatment. The administered compositions of the present invention can block the mevalonate pathway by 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60% or more in the subject as compared to a subject who is not receiving treatment.

In some embodiments, the method blocks or reduces accumulation of at least one mevalonate pathway metabolite. The administered compositions of the present invention can reduce accumulation of at least one mevalonate pathway metabolite by 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60% or more in the subject as compared to a subject who is not receiving treatment. The administered compositions of the present invention can block accumulation of at least one mevalonate pathway metabolite by 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60% or more in the subject as compared to a subject who is not receiving treatment.

In some embodiments, the method blocks or reduces accumulation of at least one mevalonate pathway toxic metabolite. The administered compositions of the present invention can reduce accumulation of at least one mevalonate pathway toxic metabolite by 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60% or more in the subject as compared to a subject who is not receiving treatment. The administered compositions of the present invention can block accumulation of at least one mevalonate pathway toxic metabolite by 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60% or more in the subject as compared to a subject who is not receiving treatment.

In various embodiments, the method replenishes cholesterol, blocks or reduces the mevalonate pathway, blocks or reduces at least one mevalonate pathway metabolite, blocks accumulation of at least one mevalonate pathway toxic metabolite, or any combination thereof.

It will be understood by those of skill in the art that numerous and various modifications can be made without departing from the spirit of the present disclosure. Therefore, it should be clearly understood that the forms disclosed herein are illustrative only and are not intended to limit the scope of the present disclosure.

Kits

The present invention also pertains to kits useful in the methods of the invention. Such kits comprise various combinations of components useful in any of the methods described elsewhere herein, including for example, materials for lowering lipid levels in a subject in need thereof (e.g., lipid-lowering drugs), and instructional material. For example, in one embodiment, the kit comprises components useful for preventing or treating a desired disease or disorder in a subject in need thereof. In another embodiment, the kit comprises the components of an assay for monitoring the effectiveness of a treatment administered to a subject in need thereof.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples therefore, specifically point out the preferred embodiments of the present invention, and are not to be construed as limiting in any way the remainder of the disclosure.

Example 1: Topical Cholesterol/Lovastatin for the Treatment of Porokeratosis: A Pathogenesis-Directed Therapy Although not bound by any particular theory, it was hypothesized that applying topical lovastatin/cholesterol could alleviate porokeratosis via replenishing and blocking accumulation of mevalonate pathway toxic metabolites (FIG. 1). As such, the application of topical cholesterol/lovastatin was tested on subjects with PPPD, DSAP and LP was tested.

Topical statin/cholesterol therapy is a pathway specific approach and may be applicable for other diseases within the mevalonate pathway. Importantly, since systemic statins have been shown to decrease severity of inflammatory skin diseases (e.g. psoriasis) (Faghihi T et al., 2011, Pharmacotherapy 31:1045-1050), and the risk for various types of cancer (Bathaie S Z et al., 2016, Curr Mol Pharmacol. 09; Abdullah M I et al., 2017, Sci Rep 7:8090; Ahmadi Y et al., 2017, Chem Biol Interact 273:273-285). This approach may be beneficial for pre-cancerous skin lesions as actinic keratosis, superficial non-melanoma skin cancer and inflammatory skin lesions including psoriasis and atopic dermatitis.

Clinical and Histologic Description of Cases

Figure 2:
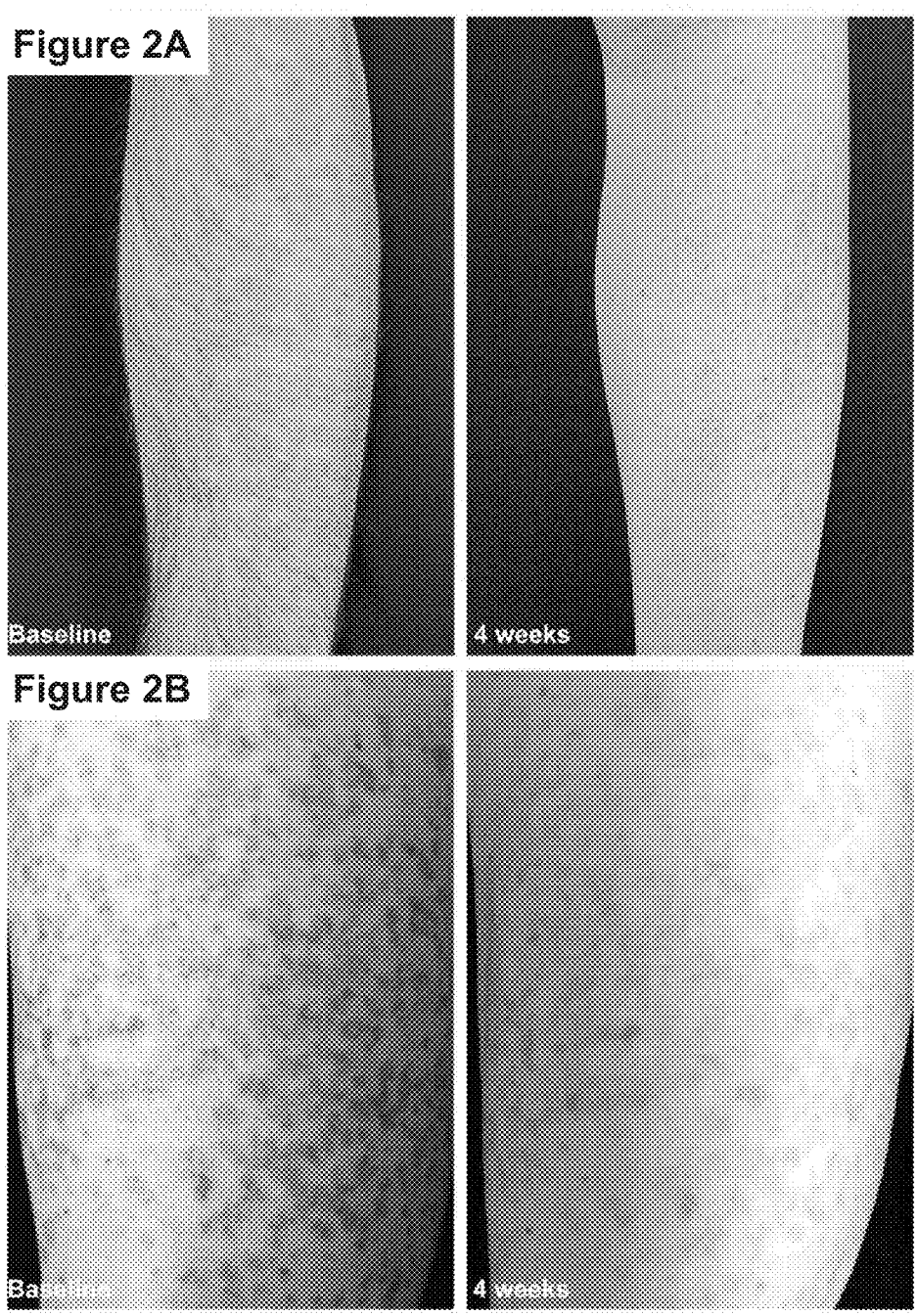
FIG. 2, comprising

Three patients with familial porokeratosis and 2 patients with LP were included in the cohort. Patients with familial porokeratosis belonged to the same family but varied in their clinical presentation. While FP100-1 had DSAP with small thin erythematous plaques surrounded by delicate cornoid lamella over sun exposed aspects of the upper and lower limbs, his sister (FP100-6) and cousin (FP100-9) had a clinical presentation of PPPD with punctate papules over pressure areas of the soles and larger purple-brown plaques with atrophic center over the extremities and more pronounced keratotic border (FIG. 2). The past medical history of FP100-9 was significant for cutaneous SCC (FIG. 3).

LP1 was a 5-year-old girl presenting with pruritic extensive whorled-linear scaly thick pink plaques over the left side of her body which were present since birth. LP2 was a 20-year-old male, presenting with whorls of linear pink verrucous papules and plaques on his upper extremities and left lower extremity that appeared at birth and became thicker over time. In all patients, a cornoid lamella was evident upon histopathologic evaluation. Subject characteristics are detailed in FIG. 3.

Genetic Analysis

Exome sequencing was conducted on affected and unaffected subjects from the FP kindred and identified a heterozygous MVD c.70+5G>A mutation (FIG. 4). The variant co-segregated with affected status and was recently found in a subject with LP we have studied where it was proved to affect MVD splicing (Atzmony et al., JAMA Derm, In Press). Paired analysis of blood and affected keratinocytes did not identify somatic mutations or loss of heterozygosity (FIG. 4). Paired WES of affected tissue and blood from LP1 and LP2 identified germline and somatic mutations. These data are detailed in the recent publication (Atzmony et al., JAMA Derm, In Press) and in FIG. 4.

Response to Therapy

FP100-1, FP100-6, FP100-9 and LP2 applied a 2% lovastatin/2% cholesterol ointment twice daily. LP1 applied a 2% lovastatin/2% cholesterol lotion. All FP patients applied the ointment on one limb (FP100-1-left upper limb, FP100-6-right shin, FP100-9-right thigh). LP1 applied the lotion on the left lower limb and LP2 applied the ointment on the left upper limb.

Response to Therapy in DSAP

Figures 5, 5A, 5B, 5C, 5D:
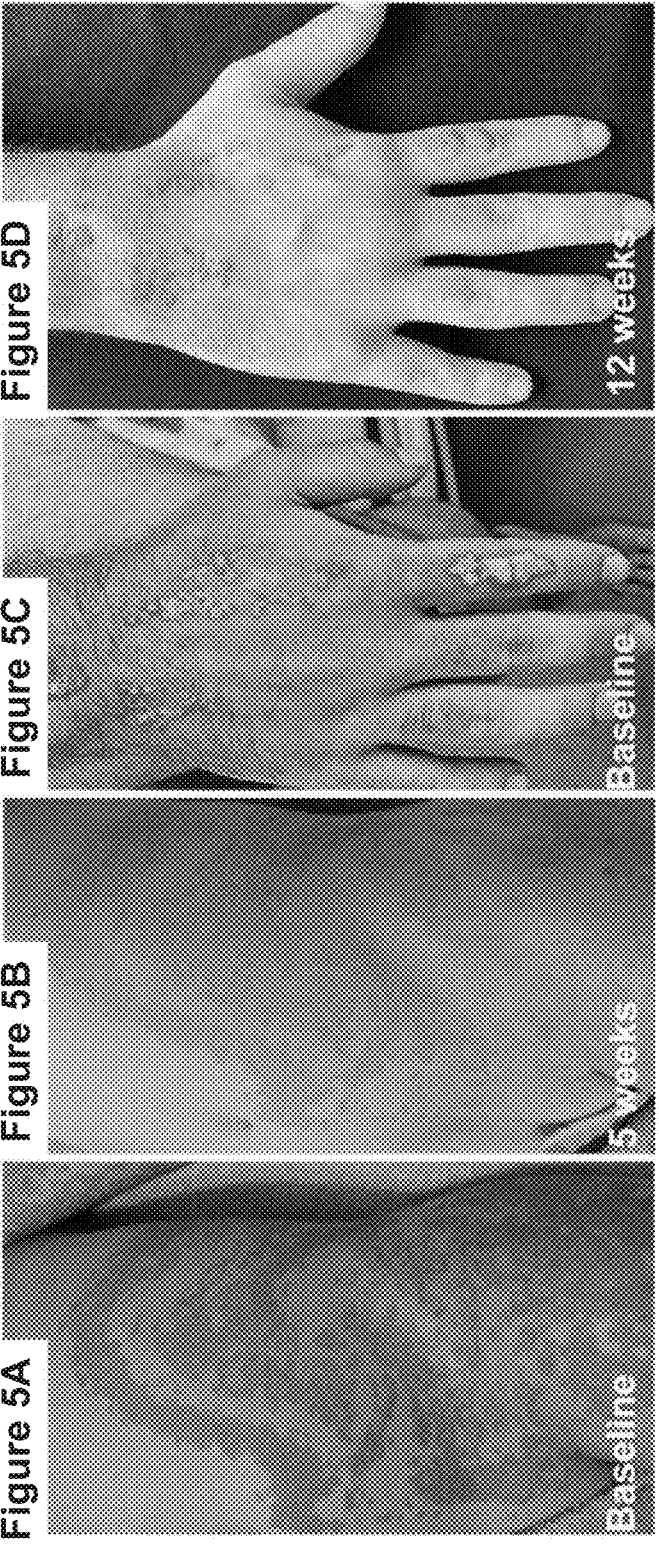
FIG. 5, comprising
FIG. 5A through FIG. 5D, depicts representative clinical improvements with topical application of lovastatin/cholesterol in subjects with LP.
Figures 6, 6A, 6B:
FIG. 6, comprising
FIG. 6A and FIG. 6B, depicts representative clinical improvement with topical application of lovastatin/cholesterol in LP.

Decrease in scaling was noted as early as 1 week in FP100-1 (FIG. 2). After 4 weeks of therapy there was marked decrease in inflammation, scaling and size of visible lesions with only residual small erythematous macules and 66% reduction of IGA score (FIG. 5). The response was maintained after 3 months of therapy. Further experiments were then performed to address the possibility that skin lesions in porokeratosis derive primarily from cholesterol depletion, but no clinical improvement after 4 weeks of treatment with twice daily application of 2% cholesterol ointment on the right upper limb was found. After 2 months of therapy the patient shows residual small erythematous macules.

Response to Therapy in PPPD

Both patients had brown-purple large atrophic plaque, hence were expected to respond slower than LP100-1 to therapy. FP100-6 was treated for 8 weeks with prominent decrease of scaling and moderate decrease in erythema. FP100-9 was treated for 6 weeks with prominent decrease of scaling and moderate decrease of erythema (FIG. 5).

Response to Therapy in LP

A remarkable decrease in scale has been noted in both patients 3-4 weeks from initiation of therapy. LP-1 also had pronounced decrease in inflammation and thickness (FIG. 5).

The advent of sophisticated genetic testing has increased the discovery of genetic changes underlying skin disorders and furthered the understanding of genetic skin diseases, introducing the opportunity of pathogenesis-directed treatment modalities. Here, for the first time, an efficient pathogenesis-directed therapy for porokeratosis is described. All included patients were genotyped prior to initiation of therapy and were proven to have MVD or PMVK mutations. Thin non-atrophic lesions in DSAP had shown excellent and fast response to lovastatin/cholesterol application, while thick and atrophic plaques in LP and PPPD had shown partial response after 4-6 weeks of therapy. Since the lesions of the included patients with LP and PPPD were thicker/ more atrophic than the lesions in the included patient with DSAP, it was predicted that they did not achieve their maximal response after 4-6 weeks of therapy and will continue to improve over time. This is corroborated by the gradual improvement over a long period of time that was seen in CHILD syndrome using the same regimen (Paller A S et al., 2011, J Invest Dermatol., 131:2242-2248).

In the mevalonate pathway, MVK, PMVK and MVD catalyze three rate limiting steps sequentially to produce isopentenyl diphosphate, a fundamental building block for the biosynthesis of isoprenoid compounds, such as sterols including cholesterol, ubiquinone, dolichols, carotenoids and some classes of isoprenylated proteins (FIG. 5)(Chang Q et al., 2008, Proteins 73:254-258). Its products are essential for regulation of gene expression, cell growth and differentiation, cytoskeleton assembly and post translational modification of proteins involved in intracellular signaling (Goldstein J L et al., 1990, Nature 343:425-430). Cholesterol is one of the components of the extracellular lipid matrix in the stratum corneum, playing an essential role in providing and maintaining skin barrier. Depletion of cholesterol has been reported to result in increased sensitivity of keratinocytes to stimuli driving apoptosis (Calay D et al., 2010, J. Invest. Dermatol., 130:1136-1145.). Premature apoptosis and dysregulated differentiation of keratinocytes have been identified in several types of porokeratosis (Shen C-S et al., 2002, Br. J. Dermatol., 147:498-502). Increased apoptosis beneath and at the cornoid lamella has been found in PMVK mutated individuals with disseminated superficial porokeratosis (Wang J et al., 2016, Sci. Rep., 6:24226), and human keratinocytes overexpressing MVK were more resilient to UVA radiation compared to MVK depleted cells (Zhang S-Q et al., 2012, Nat. Genet., 44:1156-1160). While the results in these patients support the use of topical cholesterol/lovastatin for porokeratosis, clinical trials will be necessary to systematically evaluate the efficacy of this treatment. In-vitro studies may further facilitate our understanding of the importance of other end-products depletion in the pathogenesis of the disease. In the interim, since cholesterol and lovastatin have a known safety profile and are relatively inexpensive, and since their topical application is effective in porokeratosis, the topical regimen provides a safe and effective option of therapy in porokeratosis, including in cases with extensive skin involvement.

The materials and methods are now described.

Methods

Participants and Genetic Analysis

The genetic study was approved by the Yale Human Investigation Committee and compiles with the declaration of Helsinki principles. Individual consent was obtained in writing from all participants. Genomic DNA (gDNA) was isolated via standard phenol/chloroform extraction from peripheral blood or saliva. gDNA from lesional skin was obtained from fresh full thickness skin biopsies, 1 mm cores from affected epidermis of formalin-fixed paraffin-embedded (FFPE) specimens, or cultures keratinocytes from affected skin using the DNeasy Micro Kit (Qiagen) with added deparaffinization performed for FFPE tissue. Paired analysis of whole exome sequencing (WES) of affected skin and saliva were performed, respectively, as previously described (Atzmony et al., JAMA Derm; In Press). Mutations were confirmed with Sanger sequencing.

Treatment

A 2% cholesterol/2% lovastatin ointment (n=4) or lotion (n=1) was applied twice a day on lesional skin with occlusion for the first 1-2 weeks depending on skin lesion thickness. Therapy continued for 3 months. Patients were followed-up at 3-4 weeks intervals and up to 2 months for clinical change.

Assessment of Clinical Response

Baseline clinical photography and a biopsy from affected skin were obtained.

Subjects with familial porokeratosis were evaluated using investigator global assessment scale with erythema (0-skin color, 4-very red), scaling (0-no scale, 4-pronounced keratotic edge), number of lesions (0: none, 1: 1-5 lesions, 2: 5-10 lesions, 3: 10-15 lesions, 4: >20 lesions) and size of lesions (0: no lesions, 1: <0.2 cm, 2: >0.2 and <0.5 cm, 3: >0.5 cm and <1 cm, 4:>1 cm)

All participants were photographed every visit for evaluation of improvement.

Figures 7, 7A, 7B:
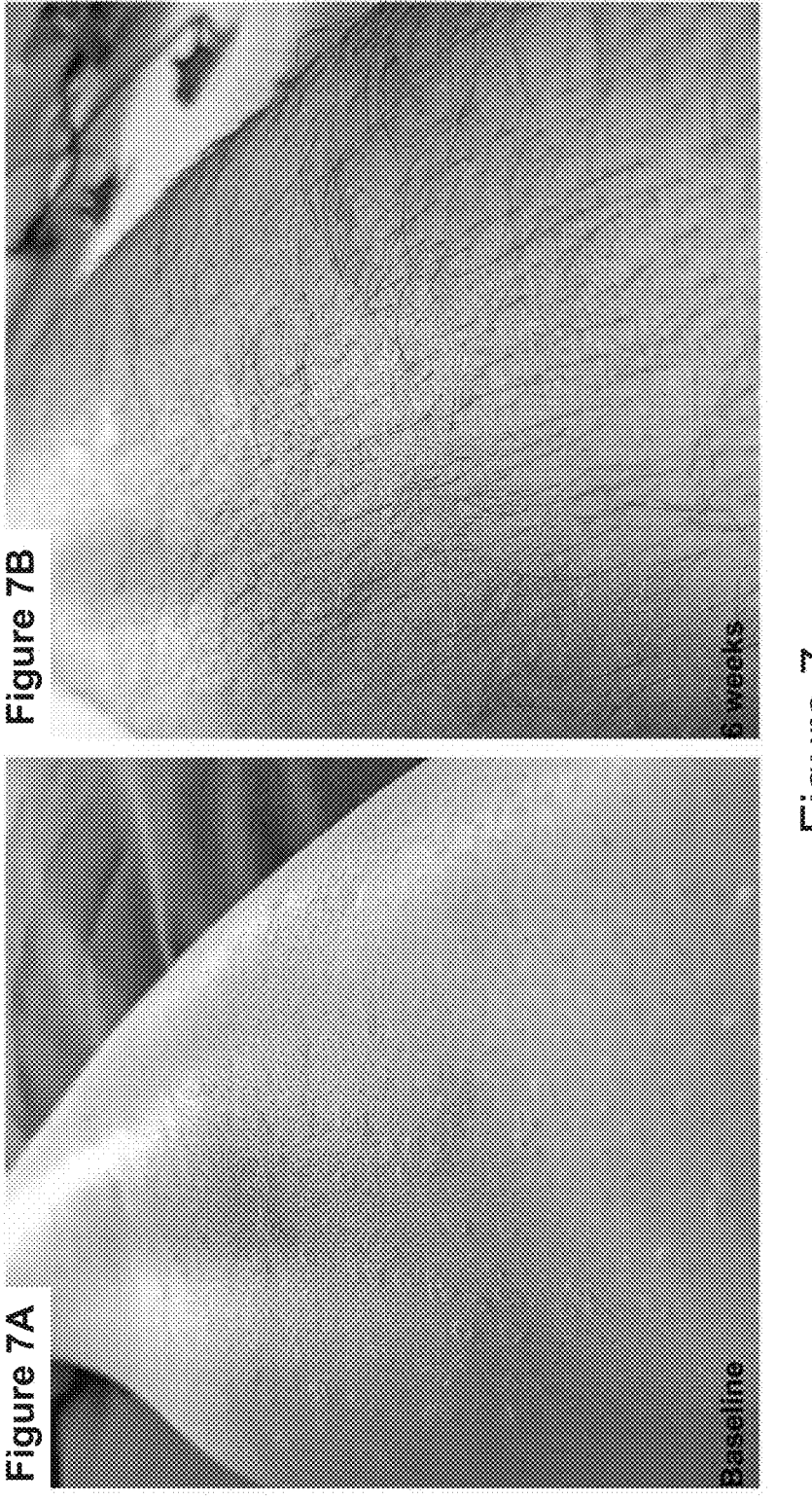
FIG. 7, comprising
FIG. 7A and FIG. 7B, depicts representative clinical improvements with topical application of lovastatin in DSAP.

Example 2: 2% Lovastatin Ointment Monotherapy as a Pathogenesis Directed Therapy for Porokeratosis In view of the above, it was hypothesized that blocking the mevalonate pathway upstream to MVD enzyme alleviates symptoms via blocking the accumulation of mevalonate pathway toxic metabolites. As such, a patient with disseminated superficial actinic porokeratosis (DSAP) with heterozygous MVD c.70+5G>A mutation applied lovastatin 2% ointment twice daily. A remarkable decrease in scale was noted after 4 weeks of therapy. After 6 weeks of therapy, the patient achieved a complete response (FIG. 7).

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

We claim:

1. A method of treating porokeratosis, the method comprising topically administering a therapeutically effective amount of a composition to a subject in need thereof,
   wherein the composition comprises a 3-hydroxy-3-methyl-glutaryl-coenzyme A HMG-CoA) reductase inhibitor, and
   wherein the porokeratosis in the subject is treated.

2. The method of claim 1, wherein the HMG-CoA reductase inhibitor is present in an amount of about 0.1% to about 25%.

3. The method of claim 1, wherein the composition further comprises at least one lipid.

4. The method of claim 1, wherein the composition is one selected from the group consisting of a gel, an ointment, a cream, an emulsion, a suspension, and any combination thereof.

5. The method of claim 1, wherein the porokeratosis is associated with a mutation selected from the group consisting of a mevalonate diphosphate decarboxylase (MVD) mutation, a mevalonate kinase (MVK) mutation, a phospho-mevalonate kinase (PMVK) mutation, a farnesyl diphosphate synthase (FDPS) mutation, and any combination thereof.

6. The method of claim 1, wherein the method comprises blocking or reducing a mevalonate pathway, blocking or reducing accumulation of at least one mevalonate pathway metabolite, or a combination thereof.

7. The method of claim 1, wherein the composition further comprises one or more pharmaceutically acceptable carriers or excipients.

8. The method of claim 1, wherein the composition is administered in combination with another therapeutic agent.

9. The method of claim 1, wherein the method is a pathogenesis-directed therapy.

10. The method of claim 1, wherein treating the porokeratosis in the subject results in one or more effects selected from the group consisting of a decrease in scaling, a decrease in erythema, a decrease in inflammation, a decrease in number of lesions, a decrease in size of lesions, a decrease in thickness of lesions, or any combination thereof.

11. The method of claim 1, wherein he HMG-CoA reductase inhibitor is selected from the group consisting of atorvastatin, fluvastatin, lovastatin, pravastatin, rosuvastatin, simvastatin, pitavastatin, and any combination thereof.

* * * * *